United States Patent [19]

Reierson

[11] Patent Number: 5,463,101
[45] Date of Patent: Oct. 31, 1995

[54] PROCESS OF MAKING LOW DIOXANE ALKOXYLATE PHOSPHATE ESTERS

[75] Inventor: Robert L. Reierson, Cranbury, N.J.

[73] Assignee: Rhone-Poulenc Inc., Monmouth Junction, N.J.

[21] Appl. No.: 347,741

[22] Filed: Dec. 1, 1994

[51] Int. Cl.$^6$ .................................................. C07F 9/09
[52] U.S. Cl. .......................................... 558/110; 558/186
[58] Field of Search ...................................... 558/110, 186

[56] References Cited

U.S. PATENT DOCUMENTS

| | | | |
|---|---|---|---|
| 3,235,627 | 2/1966 | Mansfield | 260/926 |
| 3,686,371 | 8/1972 | Hasegawa | 260/980 |
| 4,126,650 | 11/1978 | Via et al. | 260/980 |
| 4,139,485 | 2/1979 | Imokawa et al. | 252/135 |
| 4,350,645 | 9/1982 | Kurosaki et al. | 260/978 |
| 4,375,437 | 3/1983 | Katz et al. | 260/990 |
| 4,670,575 | 6/1987 | Kurosaki et al. | 558/146 |
| 4,874,883 | 10/1989 | Uphues et al. | 558/150 |
| 5,254,691 | 10/1993 | Mori et al. | 548/111 |

FOREIGN PATENT DOCUMENTS

| | | |
|---|---|---|
| 41-14416 | 8/1966 | Japan . |
| 42-06730 | 3/1967 | Japan . |
| 3188089 | 8/1991 | Japan . |

OTHER PUBLICATIONS

G. Imokawa, J. Am. Oil Chem. Soc. 56, 604 (1979).
A. Nelson & A. Toy, Inorg. Chem., 2, 775 (1963).
T. Kurosaki et al., Oil Chemistry, 39 (4), 259, (1990).
T. Glonek, et al., J. Am. Chem. Soc. 92, 7214 (1970).
T. Glonek, et al., Inorg. Chem. 13, 2337 (1974).
T. Glonek, et al., Phosphorus 1975, 157.
T. Glonek, et al., J. Am. Chem. Soc. 97, 206 (1975).
T. Glonek, et al., Phosphorus and Sulfur 3, 137 (1977).
M. Watanabe, et al., Mem. Chubu Inst. Tech., 81 (1983).
T. Kurosaki, et al., Comun. Jorn. Com. Esp. Deterg., 19, 191 (1988).
T. Khwaja et al., J. Chem. Soc. (C) 1970, 2092.
T. Kurosaki, et al., Oil Chemistry, 39 (4), 250 (1990).
W. D. Kumler and J. J. Eiler, J. Am. Chem. Soc. 65, 2355 (1943).

*Primary Examiner*—Johann Richter
*Assistant Examiner*—Michael G. Ambrose
*Attorney, Agent, or Firm*—John A. Shedden

[57] ABSTRACT

This invention relates to first stage phosphation processes which utilize a unique phosphation reagent that esterifies ethoxylated alcohols under mild reaction conditions, thus realizing reduced initial 1,4-dioxane production followed by formation of a dioxane-water azeotrope and the vacuum stripping at above about 100 torr of the azeotrope. This easily achieves product 1,4-dioxane levels below about 15 ppm based on the total ester weight.

16 Claims, No Drawings

PROCESS OF MAKING LOW DIOXANE ALKOXYLATE PHOSPHATE ESTERS

FIELD OF THE INVENTION

This invention relates to phosphation processes which have been modified to reduce the amount of 1,4-dioxane produced by reaction of an ethoxylated alcohol with a phosphation reagent while retaining the desirable low residual phosphoric acid and unreacted alcohol levels characteristic of the phosphation reaction and an expedient means to further reduce the 1,4-dioxane level to less than about 15 ppm based on the total weight of the active ester ingredient.

DESCRIPTION OF THE PRIOR ART

Because 1,4-dioxane has been reported to induce carcinomas in test animals and has a low rate of biodegradability, it is desirable to reduce the presence of this material in surfactant products that may come in intimate contact with humans or which are used in such volumes or circumstances that the release of more than trace contaminants into the environment may be possible. 1,4-Dioxane is produced as a by-product in processes in which polyethylene glycol chains are in contact with even catalytic amounts of strong acid. Fortunately, phosphoric acid and organic orthophosphoric acid esters are of relatively low acidity, thus alcohol ethoxylate phosphate mixtures are relatively stable with respect to dioxane formation under storage or use conditions. Phosphoric anhydride, however, or initial trianhydride branched intermediates formed from it by reaction with alcohol or water, are apparently sufficiently acidic under typical reaction conditions to catalyze the degradation of polyethoxylate chains and produce 1,4-dioxane.

U.S. Pat. No. 4,375,437 (Katz, et al.) teaches that the dioxane contaminant can be removed from an ethoxylated phosphate ester having residual phosphoric acid by mixing the ester with a sufficient quantity of a base, i.e. "any compound which has the ability to react with acids to form a salt, thereby neutralizing the acid". Katz, et al. theorize that dioxane is weakly bound to the residual phosphoric acid thereby precluding removal below about the 10 ppm level. Although the Katz et al. examples utilize starting phosphate esters with dioxane levels of about 119–121 ppm, commercial phosphation processes, absent multiple stripping stages, generate products that have dioxane levels at least ten and usually in excess of eighteen times that level.

Because of the broad utility of polyethoxylated alcohol phosphates, the need exists for a relatively simple, commercially economical process to provide products with low dioxane content which still retain the advantageous performance properties of the products resulting from direct phosphation with phosphoric anhydride.

SUMMARY OF THE INVENTION

The present invention relates to a two-stage process which uses a unique phosphating agent to produce, in a first stage solventless process under mild temperatures and pressures, phosphate ester compositions wherein a) monoalkyl and dialkyl esters are the major products on a molar basis; b) there are low levels of free phosphoric acid and residual alcohol; and c) the levels of dioxane are in the range of from 200 to 600 ppm. This process is followed by the second stage which comprises adding sufficient water to the first stage ester to form a dioxane-water azeotrope and removing the azeotrope under moderate temperatures and pressures. Dioxane levels of below 10 ppm are easily realized.

The major phosphate ester products of the present invention have the general formulae:

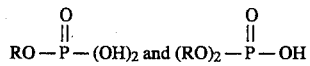

wherein R is as defined herein.

DESCRIPTION OF THE INVENTION

The instant invention relates to the production of phosphate esters with extremely low 1,4-dioxane levels and the relatively mild, commercially economical processes for producing same.

The approach of the instant invention to dioxane reduction is twofold. First, the amount of dioxane produced chemically is minimized through modification of the phosphation process such that the advantageous features of high alkylphosphate content with low free phosphoric acid and residual alcohol are still retained. Second, the reduced level of dioxane thus obtained in the above approach is further diminished through physical means by formation and removal of a water azeotrope under moderate temperature and reduced pressure such that the product composition is not significantly altered. The reduced pressure is of a magnitude such that it is economically available in a typical commercial plant, i.e., from above about 100 torr. By moderate temperatures is meant from about 70° to about 110° C.; preferably from about 80° to about 90° C.

The mechanism of dioxane formation during the conversion of ethoxylated alcohols to anionic surfactants has been studied much more extensively for alkylsulfates than alkylphosphates because of the greater severity of the problem with those compounds. This greater severity is related to the extreme acidity of the sulfation agents, commonly sulfuric anhydride ($SO_3$) and chlorosulfonic acid. By comparison, the $pK_a$ values of these acids, e.g., −10.43 for chlorosulfonic acid, −6.1 for hydrochloric acid, and −3.0 for sulfuric acid, the positive 2.15 $pK_a$ for the first ionization of phosphoric acid seems mild; more in line with organic acids such as acetic or formic acids at 4.75 and 3.75, respectively. The $pK_a$ values for the monoalkyl and dialkyl phosphate esters are comparable to but slightly less than the parent, which means that they are slightly stronger acids than phosphoric acid. (W. D. Kumler and J. J. Eiler, *J. Am. Chem. Soc.* 65, 2355 (1943)). The mechanistic principles of dioxane formation in the sulfation process, then, should also apply in the phosphation process.

The rate of dioxane formation from polyethylene oxide derivatives under acidic conditions is a direct function of acid strength, concentration of the free acid species; the degree of ethoxylation, hence the length of the polyalkylene oxide chains; and the reaction temperature. To reduce the amount of dioxane formed, of course, time and temperature should be held at minimum levels required to obtain the necessary conversion to product. The degree of ethoxylation, however, is generally dictated by the performance requirements, hence cannot be altered appreciably. The use of phosphoric anhydride as the phosphation reagent, assumed essentially necessary to obtain high conversion of alcohol with low residual free phosphoric acid, is also limiting.

By following the change in dioxane concentration during a phosphoric anhydride phosphation of a nonylphenol ethoxylate, it has been determined that it is formed predominantly during the phosphoric anhydride addition period and the first six hours of the post-addition cook period. During this cook period, the mixture changes from a slurry to a hazy liquor as the solid phosphoric anhydride dissolves as it is consumed. The decreased rate of dioxane production after this point suggests that phosphoric anhydride or the reactive intermediates initially formed from the anhydride are more active than the alkylpolyphosphate products being formed. The use of Lewis bases to complex with the aggressive acid species has been shown to result in reduced levels of dioxane in the chlorosulfation process, where only small amounts are required because the free sulfation agent is so reactive that its concentration remains low throughout the addition period. However, an amount of base sufficient to complex with the unconverted phosphoric anhydride accumulated in the slurry formed during its addition would change not only the nature of the final product from the all acid form, which could be neutralized with a base of customer choice (e.g. sodium, potassium or ammonium hydroxide, alkanol amines, etc.), to a less versatile, partially neutralized form, but also could alter the characteristics of the reaction and change the product distribution.

To solve this dilemma, the first stage of the instant process uses phosphoric acid (or polyphosphoric acid) in a manner similar to a basic complexing agent because it does not aggressively catalyze dioxane formation and is therefore a weaker acid (stronger base) than the anhydride-based species which do. Furthermore, it had been shown to be substantially incorporated into the alkylphosphate products in a process already described in Rhône-Poulenc's patent applications U.S. Serial Numbers 08/220,069 and 08/220,339 filed Mar. 30, 1994 incorporated herein by reference; and hence was not detrimental to the final product mixture. Note that the term "base" as applied to phosphoric acid in this context is in a relative sense compared to the more strongly acidic species derived directly from $P_4O_{10}$. It is not meant to include anionic salts, such as sodium phosphate.

In this first stage process, a reagent is prepared by the intimate blending of phosphoric anhydride ($P_4O_{10}$) with phosphoric acid ($H_3PO_4$) or polyphosphoric acid to produce a uniform slurry or paste. The reagent composition is from about 118 to about 131%, preferably from about 118 to 125, and most preferably from about 121 to 123% expressed as an effective equivalent percent of polyphosphoric acid. The phosphate esters are then formed by contacting the reagent paste or slurry with the organic alcohol with sufficient stirring and temperature control to dissolve the reagent in the alcohol and carry the reaction to completion. This unique phosphating agent is a direct derivative of phosphoric anhydride in which phosphoric acid is used as a blocking group. The agent may be prepared quantitatively under a wide range of times and temperatures and is stable to storage under anhydrous conditions. It dissolves more readily than phosphoric anhydride, is pumpable when warmed to reduce its viscosity, and can be added more rapidly to the alcohol without the highly exothermic heat of reaction problems characteristic of phosphoric anhydride. In contrast to the use of the commercially available 115–117% polyphosphoric acids, it is not necessary to use an excess of this phosphation reagent relative to the alcohol in order to achieve good conversion rates and low residual alcohol content. In fact, stoichiometrically equal amounts of alcohol and the phosphating reagent are most desirable. The phosphoric acid used as the blocking group is consumed in the process, hence does not contribute excessively to the residual amount.

It is preferred to limit the amount of phosphoric acid to a molar ratio of two per $P_4O_{10}$ molecule (or two phosphorus equivalents of phosphoric acid to the four phosphorus equivalents in $P_4O_{10}$). Substantially more phosphoric acid would convert the reactive branched intermediates to components of simple polyphosphoric acid, and substantially less allows an undesirably high level of the tetrahedral $P_4O_{10}$ and its first reaction product, the bicyclic phosphate, to remain. In essence, with use of the preferred 2:1 ratio, the latter two highly reactive phosphate species are converted to more controllably reactive intermediates.

Importantly, these reactive intermediates are also converted in a stable, inorganic, phosphoric acid medium, i.e., there are no organic compounds present, hence no opportunity for their $P_4O_{10}$ induced decomposition products to be produced.

This phosphation reagent is in the form of a suspension of small, "fluffy", white particles in a viscous, clear matrix. It is stirrable above room temperature and therefore pumpable. It dissolves much more readily than $P_4O_{10}$, even though the particle size is much larger, and does not produce the hard, slowly soluble, black chunks which are encountered when $P_4O_{10}$ itself is mixed into a polyethoxylated alcohol. Since much of the ring strain energy has been released, the heat of reaction is primarily that resulting from conversion of the phosphorus-oxygen-phosphorus anhydride bonds to the carbon-oxygen-phosphorus ester bonds and the hydrogen-oxygen-phosphorus acid bonds. This staged release of energy is much easier to control on a commercial process scale and the better control at lower temperatures allows minimization of undesirable by-products.

The sequence of reactant addition to the reaction is not critical. For example, the alcohol can be added to the reactor containing the phosphation reagent or the phosphation reagent can be added directly to the alcohol. As is well known in the art, addition of alcohol to $P_4O_{10}$ powder can result in a vigorous, potentially uncontrollable and hazardous reaction.

The process by which the phosphation reagent may be prepared is by contacting phosphoric anhydride ($P_4O_{10}$) with phosphoric acid ($H_3PO_4$) in a manner such that the two components may be blended into a uniform slurry or paste. The composition of the reagent exists within a narrow range. The phosphoric acid component used may be in a concentration range of from about 75% to about 117% (about 54% to about 85% $P_4O_{10}$) and is commercially available in the range of from about 85% to about 115%. The phosphoric anhydride component used is of high purity and essentially anhydrous. The narrow phosphation reagent composition range is from about 118% to about 131% (expressed as an effective equivalent percent polyphosphoric acid) preferably from about 118%–125% and most preferably from about 121%–123%.

Neither the time nor the temperature of the process for the manufacture of the phosphation reagent is critical. The time should be at least the minimum required to obtain a uniform mixture in which the $P_4O_{10}$ powder is thoroughly wetted by and blended with the phosphoric acid. The order of addition is not critical and can be adapted to the available equipment.

The initial temperature may begin at ambient room temperature and range to 180° C. as dictated by temperature control, stirring and pumping capabilities of the reactor and associated equipment. However, prolonged periods at elevated temperatures should be avoided.

The phosphation reagent is stable to storage under reasonable conditions as long as anhydrous conditions are maintained in the storage container. Like all condensed (dehydrated) phosphoric acid materials, the phosphation reagent is hygroscopic and absorption of air moisture will result in a change in the composition.

With respect to the use of the phosphation reagent in a phosphation esterification reaction, as previously noted, the alcohol may be added to the phosphation reagent or the reagent may be added to the alcohol within the mixing and temperature constraints of the reactor in accordance with standard practices well known in the art. It is not necessary to stage the reaction. Simple combination of the alcohol and the phosphation reagent in the proper stoichiometric molar ratio of four alcohols per mole $P_4O_{10}$, plus an additional mole for each mole of phosphoric acid used to form the reagent, i.e. equimolar alcohol-phosphorus, is all that is required. A moderate excess of alcohol does not significantly change the monoalkyl phosphate to dialkyl phosphate ratio (MAP:DAP) but will contribute to a higher residual alcohol content in the final ester product. In some applications, this may be desirable and, as such, may be a serendipitous characteristic of the process. Use of significantly less than the stoichiometric amount of alcohol retards the dissolution rate and leaves an undesirable high level of pyrophosphate intermediates which would have to be converted by addition of additional alcohol and/or water.

The organic hydroxy compounds which can be phosphated by the phosphation reagent of this invention are of the formula $RO\{C_nH_{2n}O\}_xH$ wherein R is selected from the group consisting of a saturated or unsaturated aliphatic $C_1$–$C_{30}$ straight or branched carbon chain, a phenyl, a mono-,di-,or tri-substituted phenyl, a phenyl $C_1$–$C_6$ alkyl and a mono-,di-,or tri-substituted phenyl $C_1$–$C_6$ alkyl, wherein the phenyl substituent group(s) each have a total of 1 to 30 carbon atoms, and wherein each substitution can be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x is from 2 to 100.

As noted above, the times and temperatures required for reacting the phosphation reagent with the alcohol can be easily determined by those skilled in the art and are principally a function of the mixing, pumping, and temperature control capabilities of the reactor and associated equipment. During the initial blending step, preferably, the initial temperature would be high enough to promote easy mixing and dissolution, i.e. from about ambient room temperature to about 80° C. Similarly, the cook temperature would be dictated by the need to obtain reasonably short cycle times without excessive discoloration of the product; typically from about 75° C. to about 100° C. Typical reaction times are from about 1 to about 12 hours. Times from about 3 to about 11 hours are preferred, and from about 4 to about 8 most preferred to prevent product degradation and color formation.

During the reaction process, a point is reached at which the principal remaining phosphate intermediates are the relatively unreactive pyrophosphates, which together with the unconverted alcohol are at low concentration. Since little additional beneficial change in the composition can be achieved by prolonged heating, it is expedient to add a small amount of water to complete the conversion of the pyrophosphates to orthophosphates. Upon completion of this step, the liquor is customarily cooled slightly and hydrogen peroxide is added to reduce the color.

In an alternative process, the phosphation reagent composition can be prepared in-situ and used to prepare the first stage phosphate ester composition of this invention. In this in-situ process, the reagent is prepared by the intimate blending and preferential reaction of phosphoric acid ($H_3PO_4$) dissolved in an alcohol ($RO$-$\{C_n$-$H_{2n}O\}_x$-$H$) as described above with phosphoric anhydride ($P_4O_{10}$). This reagent, formed in the alcohol medium, ultimately reacts with the alcohol to produce the phosphate ester composition of the first stage of this invention.

The essence of the unexpectedness of this alternative first stage process lies in the discovery that the highly selective phosphation reagent can be prepared and utilized during a single reaction stage phosphation process by first preparing a solution of phosphoric acid dissolved in alcohol(s) under essentially non-reactive temperature conditions; and then intimately blending an appropriate amount of phosphoric anhydride into the acid-alcohol solution with sufficient stirring and temperature control to form the phosphation reagent; and finally, carrying out the phosphation reaction to completion.

Apparently, under appropriate temperature conditions, the phosphoric anhydride reacts with the —OH group of the phosphoric acid preferentially as the anhydride is added to the acid-alcohol solution to form the phosphate group-blocked phosphation reagent which then subsequently reacts with the alcohol in substantially the same manner as the phosphation reagent would have reacted had it been prepared in a separate process prior to addition to the alcohol.

In the preparation of the acid-alcohol reactant solution, the sequence of addition is not critical, but for good mixing and temperature control, if standard polyphosphoric acid (115%) were used, addition of the acid to the alcohol would be preferred. The important criterion is that the phosphoric acid be dissolved in the organic alcohol under essentially non-reactive conditions. Heat can be applied to expedite dissolution of the acid in the alcohol and, preferably, the temperature of the solution should not exceed about 65° C.; more preferably, not exceed about 45° C. and the times at temperatures beyond the more preferred range should be minimized.

Since i) it is desirable to minimize alcohol phosphation by the phosphoric acid prior to the $P_4O_{10}$ addition, and ii) the reagent formation is an exothermic reaction; the acid alcohol solution is preferably cooled to below 45° C. prior to the addition of the phosphoric anhydride and kept preferably below about 60° C. during the phosphoric anhydride addition.

As mentioned previously, the addition of alcohol to $P_4O_{10}$ powder can result in a vigorous, uncontrollable, potentially hazardous reaction. Therefore, the $P_4O_{10}$ is preferably added to the acid-alcohol solution and not the other way around.

The temperature of the alcohol with the in-situ prepared phosphation reagent admixed is then raised to initiate and complete the phosphation reaction. The times and temperatures required for reacting the phosphation reagent with the alcohol can be easily determined by those skilled in the art and are primarily a function of the mixing, pumping, and temperature control capabilities of the reactor and associated equipment. Preferably, the temperature range of the reaction should be from about 75° C. to about 100° C.; most preferably, from about 79° C. to about 85° C. This cooler temperature is essentially dictated by the need to obtain reasonably short reaction times without excessive discoloration of the product.

Typical reaction times are from about 1 to about 12 hours.

Times from about 3 to about 11 hours are preferred, and from about 4 to about 8 most preferred to prevent product degradation and color formation.

The formation of the solution; temporary storage of the solution; formation of the phosphation reagent; and the phosphation reaction should preferably take place under anhydrous conditions.

The characteristics of the above processes for the formation of the phosphation reagent and its reaction with an alcohol to produce a phosphate ester product mixture suggest that the processes would be adaptable to continuous processes run either concurrently or consecutively.

The above two first stage approaches were effective, as shown in the following examples, in achieving a nearly six-fold reduction in the initial dioxane levels of from 1710 ppm in the control run, in which a nonylphenol-9 mole ethoxylate was phosphated with phosphoric anhydride in the laboratory using a standard prior art procedure, to only 290 ppm in the run using the preferred phosphoric acid mediated phosphoric anhydride phosphation reagent under similar time and temperature conditions. The first stage processes of the instant invention realize dioxane levels of less than 600 ppm, preferably less than 250, and most preferably less than 100. Dioxane levels in similar, commercially produced nonylphenol 9-mole ethoxylate phosphates are frequently in the 2000±500 ppm range.

The levels of dioxane obtained by the first stage process of this invention are still an order of magnitude higher than desired so a final reduction is made to remove the residual dioxane by codistillation of the initial reaction product with water, i.e. the azeotrope so formed, under moderate temperatures and pressures.

In a series of experiments, dioxane was removed from a lauryl 3-mole ethoxylate phosphate (residual dioxane about 425 ppm) by codistillation with water at 70° C. and various pressures. The experiments showed the value of adding small amounts of water and the reduction limit of 186 ppm dioxane content practically attainable at 70°–76° C. and 160 torr. Reduction of the pressure to 60 torr at 70° C. with a low nitrogen flow and additional water achieved a dioxane reduction to 8 ppm, but this is well below the vacuum capabilities of most commercial plants. In further laboratory testing, the use of higher temperature (90° C.) and much better vacuum (10 torr), was effective in reducing the dioxane level in nonylphenol 9-mole ethoxylate phosphates having initial dioxane levels of about 425 ppm to about 10 ppm over a six hour period.

Neutralization of the acid phosphate esters with sodium hydroxide with or without added water allowed dioxane levels below 1 ppm to be achieved because the higher, more neutral pH significantly reduced the rate of continuing dioxane production which, by competing with the rate of removal, had maintained the slightly higher levels in the finished product. (M. M. Katz, M. M. Hashem, and C. P. Talley, U.S. Pat. No. 4,375,437, Mar. 1, 1983)

The problem, therefore, was not whether or not the dioxane could be reduced to less than about 15 ppm, but how could it be done most expediently and in a commercially acceptable, i.e. cost-effective environment without significantly altering the product, for instance, by neutralizing it to a salt.

The second stage of the instant process, supplemental to the chemical modification in the first stage which achieved nearly an order of magnitude reduction in dioxane content compared to product from a standard phosphoric anhydride process, was necessary to achieve the additional order of magnitude reduction needed to reach the low dioxane, i.e., the less than 15 ppm range (based on the total weight of the ester) desired. As mentioned above, such levels can be achieved by the use of high vacuum levels of 10 torr. The examples herein provided demonstrate that, unexpectedly, similar dioxane levels can be obtained by the use of the more economically attainable vacuum levels of a typical commercial plant of above about 100 torr. An added advantage of using the higher pressure is that the water dioxane vapors can be more effectively condensed, hence more easily collected for transfer to water treatment facilities with less loss through the system as vapor. The boiling point for water, for example, is about 54° C. at 110 torr vs. about 11° C. at 10 torr. Additionally, the reduction achieved by the initial, chemically modified process significantly reduces the demands upon the physical reduction step and the amount of the dioxane waste stream to be treated.

The ultimate test of the validity of a process change to remove an undesirable by-product is whether or not the altered product still works in the application. In this case, the more environmentally acceptable, low dioxane product was compared to a commercial standard used as a surfactant component to improve the delignification process in preparing wood chips for pulp and paper manufacture. The experimental data show that the product from this process performed at least as well as the standard, confirming that the process improved its environmental acceptability while retaining its desirable performance characteristics and method of use.

The processes and utility of the present invention are demonstrated in detail in the following, non-limiting working examples.

Example 1

Prior Art Phosphoric Anhydride Process—Control

An oven pre-dried reactor system consisting of a three liter, four neck, round bottom flask equipped with a paddle stirrer, thermometer, argon inlet and outlet through a condenser capped Dean Stark trap and silicone fluid bubbler was assembled while warm and charged with 2273.53 g. nonylphenol ethoxylate (mol. wt. 612; 8.9 ethylene oxide units (average)) against a positive flow of inert gas. Phosphoric anhydride ($P_4O_{10}$), 215.73 g., was added from a precharged flask through a flexible connector under argon atmosphere. The liquor temperature rose from 25° C. to 55° C. during the 50 minute addition period. The dioxane concentration increased from 26 ppm for the alcohol to 524 ppm at the end of the addition period.

The slurry was then heated to 80° C. and held there for eight hours. The dioxane content increased quickly at first, from 1330 ppm to 1410 ppm, and to 1575 ppm for the first three hourly samples, then only 1690 for the five hour and 1710 ppm for the final sample.

Deionized water, 166.57 g., was added to the 80° C. solution. After 30 minutes, the evacuation of the headspace was initiated. The pressure was reduced slowly to avoid complications from foaming or excessively vigorous boiling. Water condensation began at a pressure of about 300 torr and condensate collection began thirty minutes into the operation at 190 torr and a liquor temperature of 77° C. The pressure was quickly cycled to atmospheric and back each hour for sampling. Gas chromatographic analysis of these samples showed that the dioxane level decreased to 1120 ppm at 138 torr, 420 ppm at 110 torr, 210 ppm at 107 torr and 130 ppm, still at 107 torr, over the first four hours. The temperature decreased to a 70° C. minimum during the first hour, but was returned to 80° C. by the third sampling. The condensate collection had ceased about ten minutes before the four hour sample and heating at 110 torr was continued for 30 minutes after it. Analysis showed the dioxane level to be unchanged, however, so the operation was stopped. The dioxane content of the final sample, after hydrogen peroxide bleaching and transfer to storage was still about 130 ppm. Analysis of the gross product composition showed it to be 1.0 weight percent phosphoric acid, 53.4 weight percent monoalkyl phosphate, 41.0 weight percent dialkyl phosphate and 4.6 weight percent nonionic components.

EXAMPLE 2

Rhône-Poulenc's "In-situ Phosphation Reagent Process", U.S. Ser. No. 08/220,339, filed Mar. 30, 1994 with Removal of 1,4 Dioxane as the Water Azeotrope Under Reduced Pressure A two liter, four neck flask equipped and dried as in Example 2 was similarly charged with 1201.26 g. nonylphenol ethoxylate (mol. wt. 612), followed by 103.95 g. polyphosphoric acid, 115%, added over a 12 minute period. The liquor temperature rose to a maximum of 35° C. Stirring was continued for thirty minutes to assure dissolution of the acid, during which time the temperature dropped to 34° C. The phosphoric anhydride, 52.69 g., was then sifted into the stirred solution over a 20 minute period. The resulting 42° C. slurry was stirred for 15 minutes, during which time the temperature rose to 45° C., and sampled for analysis. The dioxane content was 80 ppm (compared to over 500 ppm at the end of the $P_4O_{10}$ addition in Example 1).

The slurry was then heated to 80° C. over an eighty minute period, sampled, and maintained at 80° C. with hourly sampling for seven hours. The dioxane levels showed a similar but more slowly increasing rate, i.e. at 123 ppm at the beginning of the 80° C. period; 165 ppm at 1 hour; 199 ppm at 3 hours, and finally 290 ppm at the seventh hour. This result is 17% of, or about one-sixth, the 1710 ppm level of the product of Example 1.

After an additional fifteen minutes, 85.67 g. deionized water was added and after an hour, the pressure was slowly decreased. Because of the fairly rapid reduction in pressure, slight foaming was encountered but controlled in the range of 200 torr, 78° C. liquor. Five minutes into the operation, the condensate began to collect (167 torr, 74° C.). The liquor temperature decreased to 70° C. during the first hour with the pressure stabilizing at 110 torr. Analysis of samples taken as before showed the dioxane content to be 70 ppm at 110 torr; 30 ppm at 113 torr after the second hour; 21 ppm at 108 torr after the third hour, and less than the 15 ppm analytical detection limit after the fourth hour, with the liquor temperature back to 83° C. The solution was not bleached.

The in-situ process thus produced less dioxane and that lower amount which was produced was more completely removed from the product mixture, i.e. to below the 15 ppm limit of detection in a commercially reasonable four hour stripping period at a readily accessible commercial plant reactor pressure of about 110 torr. The gross product composition was 3.0 weight percent phosphoric acid, 70.7 weight percent monoalkyl phosphate, 17.5 weight percent dialkyl phosphate and 8.8 weight percent nonionic components.

EXAMPLE 3

Rhône-Poulenc's "In-situ Phosphation Reagent Process", U.S. Ser. No. 08/220,339, filed Mar. 30, 1994 with Continuous Water Addition During Stripping Operation To demonstrate latitude in the process, the apparatus described in Example 2 was charged with 1171.17 g. nonylphenol ethoxylate (mol. wt. 612) and 101.64 g. polyphosphoric acid, 115%, was added over a 25 minute interval. The solution was warmed by heat lamp to 50° C. The phosphoric anhydride, 51.07 g., was sifted into the stirred, unheated solution over a ten minute interval with the liquor temperature reaching a 63° C. maximum six minutes thereafter. The slurry was then heated by oil bath to stabilize at 80°–82° C. Samples removed after 100 minutes and 16 hours reaction period were determined to contain 210 ppm and 290 ppm dioxane, respectively.

A pressure equalizing addition funnel containing 145.03 g. deionized water was set in the flask neck through which the phosphoric anhydride had been added. Over the next 4-½ hours, three approximately 25 ml volumes of water were added just prior to the reductions in pressure following the sampling operations at 90 minute intervals. The dioxane levels decreased to 160 ppm at 1-½ hours; 86 ppm at 3 hours; and 33 ppm at 4-½ hours. The temperature range was 74°–80° C. and the minimum pressure was 110 torr. The final water charge was added (the total of four portions of water was 96.99 g.); the liquor warmed to 89° C.; and the pressure decreased to 105 torr. The sample taken after an hour contained 9 ppm dioxane. No additional water was added. Over the next 90 minutes, the temperature was allowed to rise to 92° C. and the pressure lowered to 98 torr. The boiling essentially ceased and only 1 ml of water had collected in the Dean-Stark trap. The resulting level of dioxane was only reduced to 6 ppm. Heating for another 85 minutes at 92° C. and 108 torr did not change the dioxane content.

In this Example 3, the sample sizes were increased for the gas chromatography headspace analysis in order to obtain a lower detection limit. At this new level of sensitivity, i.e., about 1–2 ppm, an interfering trace component was discovered as a shoulder on the normally sharp dioxane peak which could have contributed up to 4–5 ppm to the originally measured values. This was not a problem for the higher levels, but could have caused a significant error in the lower levels. The values, however, were not corrected for this interference because of the uncertainty of its magnitude. If it had been applied, the final dioxane value in this example would have been near the detection limit.

This example demonstrates that water can be added in increments to achieve the same result as a single addition at the beginning of the vacuum stripping period. Finishing the stripping at 92° C., instead of 80° C., with a slightly lower pressure did accomplish a modest further decrease in the dioxane level from 9 to 6 ppm (5 to 2 ppm dioxane if the aforementioned correction for the impurity is taken into account).

Low pressure steam or hot condensed water might alternately be used in the azeotropic removal of the dioxane, but care should be exercised to not expose the product to prolonged contact with temperatures above the 80°–97° C. investigated in order to minimize product degradation.

Example 4

Effect of Higher..Acid Ratio; Substitution of 105% Polyphosphoric Acid

The previously identified Rhône-Poulenc applications demonstrated that the entire commercial range of polyphosphoric acid concentrations, from 85% to 115% are effective and can be used to prepare the phosphation reagent used in of the first stage of this invention. To demonstrate that similar flexibility exists with regard to the lower dioxane process advantage claimed herein, 105% polyphosphoric acid was substituted for the 115% used in the previous Examples 2 and 3, and the molar amount of acid was increased; that is, the effective composition of the total phosphation reagent was reduced from about 122.75% to 121.60%.

By the procedure in Example 3, 68.82 g. 105% polyphosphoric acid was added to 1045.50 g. nonylphenol ethoxylate (molecular weight 612) in nine minutes. The liquor temperature rose from 21° C. to 28° C. Phosphoric anhydride, 68.97 g., was then added over a 20 minute period. The liquor temperature reached a maximum of 48° C. in ten minutes, after which time, it was heated to 80° C. and maintained at 80°–81° C. for 22 hours.

The rate of dioxane generation was considerably lower in this example than that of Examples 2 and 3. The sample taken 12 minutes after the phosphoric anhydride addition analyzed for only 44 ppm dioxane (the alcohol starting material contained 13 ppm dioxane). Two and one half hours at 80° C. were required to reach 80 ppm dioxane and four hours to reach a level of 90 ppm. The final dioxane content after 22 hours at 80°–81° C. was 137 ppm.

Example 5

Effect of Lower Acid Ratio

To illustrate that some benefit can be obtained by adding less than the optimum ratios claimed in the Rhône-Poulenc applications, the amount of 105% polyphosphoric acid was reduced to give a phosphation reagent with a composition of 129.9% expressed as polyphosphoric acid equivalent.

By the procedure in Example 4, 32.34 g. 105% polyphosphoric acid was added to 1,044.12 g. nonylphenol ethoxylate (molecular weight 612) followed by 97.09 phosphoric anhydride. The temperature stabilized at 57° C. before heat was applied to raise it to 80° C. After 10 hours at 80°–81° C., approximately 35 ml. deionized water was added and the solution stirred for 90 minutes. The pressure was then reduced to 110 torr and maintained with stirring at 80°–84° C. for an hour. The pressure was returned to atmospheric, the liquor sampled, 25 ml. Water was added and the stripping operation resumed for a second hour. This hourly cycle was repeated two more times with the maximum temperature being raised slowly from 84° C. to 86° C., and 87° C. The final hour of the five hour vacuum stripping period was run at 87° C. to 97° C.

The dioxane level of the product before stripping was 560 ppm, thus showing a higher dioxane level as a result of the lower phosphoric acid to $P_4O_{10}$ ratio, but still one substantially improved over Example 1. The dioxane levels in the hourly samples during the stripping operation were 270, 70, 16, 7, and 4 ppm respectively, demonstrating that extremely low dioxane levels can be attained at reasonable vacuum even in the presence of residual phosphoric acid and with a brief excursion to near 100° C. to finish the stripping process.

The gross product composition was 2.3 weight percent phosphoric acid, 66.4 weight percent monoalkyl phosphate, 29.6 weight percent dialkyl phosphate and 1.7 weight percent nonionic.

Example 6

Performance Evaluation in Wood Chip Delignification

Nonylphenol - 8.9 POE ethoxylate phosphates prepared by a conventional phosphoric anhydride process have been shown to be useful surfactants to improve the efficiency of wood chip delignification processes. To confirm that the product prepared by the process of Example 2 was also effective, southern pine wood chips were digested in a caustic liquor containing 0.1 weight percent of the phosphate. The performance was evaluated in terms of the yield of pulp, the amount of the digested product which did not break easily into a fiber product (percent rejects on pulp) because of retained lignin residues, and a Kappa Number, which is an indication of the oxidizable lignin residues retained in the pulp.

TABLE I

| Experiment | Pulp Yield (%) | Rejects on Pulp (%) | Kappa Number |
|---|---|---|---|
| Control (no surfactant) | 58.1 | 11.9 | 101.0 |
| Commercial Phosphate, 0.1% (as in Example 1) | 56.3 | 8.3 | 87.3 |
| Subject Phosphate, 0.1% (Example 2) | 55.8 | 8.0 | 83.7 |

The results summarized in Table I show that at a use level of two pounds per ton of wood chips (0.1 weight percent), both phosphates increase the net yield of pulp and improve its quality (lower Kappa Number) so that less bleach is required to prepare the pulp for paper manufacture.

Thus, two environmental advantages are gained by the use of the processes of this invention: firstly, a reduction in the bleach by-products and secondly, a substantial reduction in dioxane in the final product.

I claim:

1. A process for the production of low 1,4-dioxane, phosphoric acid esters comprising
    A. reacting
        a) at least one alcohol of the formula I RO{ $C_nH_{2n}O$ }$_x$H    (I) 

wherein R is selected from the group consisting of a saturated or unsaturated aliphatic $C_1$–$C_{30}$ straight or branched carbon chain, a phenyl, a mono-, di-, or tri-substituted phenyl, a phenyl $C_1$–$C_6$ alkyl and a mono-, di-, or tri-substituted phenyl $C_1$–$C_6$ alkyl, wherein the phenyl substituent group(s) each have a total of 1 to 30 carbon atoms, and wherein each substitution may be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x is from 2 to 100; with
        b) a slurry or paste reagent composition produced by intimately mixing an effective amount of phosphoric anhydride with from about 75 weight percent to about 117 weight percent phosphoric acid, said reagent composition having an effective equivalent polyphosphoric acid weight percent of from about 118 to 131;

B. Adding an effective amount of water to form a dioxane-water azeotrope; and

C. vacuum stripping said azeotrope above about 100 torr.

2. A process for the production of low 1,4-dioxane, phosphoric acid esters comprising the steps of:

A. intimately blending at from about ambient room temperature to about 80° C. for mixing and dissolution
   a) at least one alcohol of the formula I $RO\{C_nH_{2n}O\}_xH$ (I)

wherein R is selected from the group consisting of a saturated or unsaturated aliphatic $C_1$–$C_{30}$ straight or branched carbon chain, a phenyl, a mono-, di-, or tri-substituted phenyl, a phenyl $C_1$–$C_6$ alkyl and a mono-, di-, or tri-substituted phenyl $C_1$–$C_6$ alkyl, wherein the phenyl substituent group(s) each have a total of 1 to 30 carbon atoms, and wherein each substitution may be a saturated or unsaturated straight or branched carbon chain, a phenyl, an alkyl phenyl, a phenyl alkyl or an alkyl phenyl alkyl group; wherein n is from 2 to 4 and may be the same or different for each alkylene oxide unit; and wherein x is from 2 to 100; with
   b) a slurry or paste reagent composition produced by intimately mixing an effective amount of phosphoric anhydride with from about 75 weight percent to about 117 weight percent phosphoric acid, said reagent composition having an effective equivalent polyphosphoric acid weight percent of from about 118 to 125;

B. reacting said blend at from about 75° C. to about 100° C. for a reaction time of from about 1 to about 12 hours;

C. adding an effective amount of water to form a dioxane-water azeotrope; and

D. vacuum stripping at from about 70° C. to about 110° C. said azeotrope above about 100 torr.

3. The process of claim 1 wherein the reagent composition has an effective equivalent polyphosphoric acid weight percent of from about 121 to about 123.

4. The process of claim 1 wherein the alcohol is reacted with an equimolar amount of the slurry or paste reagent composition.

5. The process of claim 1 wherein the vacuum stripping occurs from about 80° to about 90° C.

6. The process of claim 1 wherein an effective amount of water is added to the reaction prior to the vacuum stripping to hydrolyze residual pyrophosphate intermediates.

7. The process of claim 2 wherein the alcohol is an ethoxylated nonyl phenol.

8. The process of claim 2 wherein the alcohol is a tristyrylphenol ethoxylate.

9. A process for the production of low 1,4-dioxane phosphoric acid esters comprising:

A. preparing a phosphoric acid-alcohol reactant solution by
   i) dissolving
   a) from about 75 weight percent to about 117 weight percent phosphoric acid in
   b) at least one alcohol medium of the formula I $RO\{C_nH_{2n}O\}_xH$ (I)

wherein R is selected from the group consisting of a saturated or unsaturated aliphatic $C_1$–$C_{30}$ straight or branched carbon chain, a phenyl, a mono-, di-, or tri-substituted phenyl, a phenyl $C_1$–$C_6$ alkyl and a mono-, di-, or tri-substituted phenyl $C_1$–$C_6$ alkyl, wherein the phenyl substituent group(s) each have a total of 1 to 30 carbon atoms, and wherein each substitution may be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x is from 2 to 100;

B.
   i) intimately blending into said reactant solution and
   ii) reacting the phosphoric acid in said reactant solution with a stoichiometrically effective amount of phosphoric anhydride to produce in-situ a phosphation reagent having an effective equivalent polyphosphoric acid weight percent of from about 118 to 131; and C. reacting the phosphation reagent so produced with the alcohol medium at from about 75° C. to about 100° C. for a reaction time of from about 1 to about 12 hours:

D. adding an effective amount of water to form a dioxane-water azeotrope; and

E. vacuum stripping said azeotrope above about 100 torr.

10. The process of claim 9 wherein
i) the phosphation reagent has an effective equivalent polyphosphoric acid weight percent of from about 118 to about 125; and
ii) the vacuum stripping occurs at from about 70° C. to about 110° C.

11. The process of claim 9 wherein:
i) the temperature at which the phosphoric acid is dissolved in the alcohol does not exceed 65° C.; and
ii) the temperature at which the phosphoric anhydride is blended and reacted with the phosphoric acid in the alcohol medium does not exceed 60° C.

12. The process of claim 9 wherein the phosphation reagent has an effective equivalent polyphosphoric acid weight percent of from about 121 to 123.

13. The process of claim 10 wherein the vacuum stripping occurs from about 80° to about 90° C.

14. The process of claim 9 wherein an effective amount of water is added to the reaction prior to vacuum stripping to hydrolyze residual pyrophosphate intermediates.

15. The process of claim 10 wherein the alcohol is an ethoxylated nonyl phenol.

16. The process of claim 10 wherein the alcohol is a tristyrylphenol ethoxylate.

* * * * *